US009855409B2

(12) United States Patent
Avevor (10) Patent No.: US 9,855,409 B2
(45) Date of Patent: Jan. 2, 2018

(54) DEVICE FOR INDEPENDENTLY INFLATING, DEFLATING, SUPPLYING CONTRAST MEDIA TO AND MONITORING UP TO TWO BALLOON CATHETERS FOR ANGIOPLASTY

(71) Applicant: Philip Avevor, Jacksonville, FL (US)

(72) Inventor: Philip Avevor, Jacksonville, FL (US)

( * ) Notice: Subject to any disclaimer, the term of this patent is extended or adjusted under 35 U.S.C. 154(b) by 0 days.

(21) Appl. No.: 14/868,362

(22) Filed: Sep. 28, 2015

(65) Prior Publication Data

US 2016/0015947 A1 Jan. 21, 2016

Related U.S. Application Data

(63) Continuation-in-part of application No. 14/224,094, filed on Mar. 25, 2014, now Pat. No. 9,144,668.

(51) Int. Cl.
*A61M 25/10* (2013.01)

(52) U.S. Cl.
CPC ...... *A61M 25/104* (2013.01); *A61M 25/1018* (2013.01); *A61M 25/10185* (2013.11); *A61M 25/10187* (2013.11); *A61M 25/10181* (2013.11); *A61M 25/10184* (2013.11); *A61M 2205/3331* (2013.01)

(58) Field of Classification Search
CPC ...... A61M 2205/3331; A61M 25/1018; A61M 25/10184; A61M 25/104
See application file for complete search history.

(56) References Cited

U.S. PATENT DOCUMENTS

2011/0166547 A1* 7/2011 Baumbach ............. A61K 31/00
604/509

* cited by examiner

*Primary Examiner* — Kevin C Sirmons
*Assistant Examiner* — Deanna K Hall
(74) *Attorney, Agent, or Firm* — Mark Young, PA (57) ABSTRACT

An adaptable inflation device for up to two balloon catheters for angioplasty includes a plurality of three port valves controlling flow to two fluid channels each coupled at an outlet to a balloon catheter for angioplasty. A single in line pressure gauge, which may be removable, monitors pressure of each channel. Each balloon catheter may be inflated and deflated, sequentially inflated, simultaneously inflated, sequentially deflated, simultaneously deflated, inflated to the same pressures, inflated to different pressures, partially deflated, and fully deflated.

18 Claims, 11 Drawing Sheets

DEVICE FOR INDEPENDENTLY INFLATING, DEFLATING, SUPPLYING CONTRAST MEDIA TO AND MONITORING UP TO TWO BALLOON CATHETERS FOR ANGIOPLASTY

RELATED APPLICATION

This application is a continuation in part and claims the benefit of priority of U.S. nonprovisional application Ser. No. 14/224,094 filed Mar 25, 2014, the entire contents of which are incorporated herein and made a part hereof.

FIELD OF THE INVENTION

This invention relates to angioplasty, and, more particularly, to an adaptable fluid dispensing and inflation device for balloon angioplasty for independently inflating and deflating up to two separate balloons using a single plunger and gauge and independently supplying radiopaque contrast medium through two catheters.

BACKGROUND

Angioplasty entails mechanically widening narrowed or obstructed arteries, such as arteries obstructed from atherosclerosis. An empty and collapsed balloon on a guide wire, known as a balloon catheter, is fed into a vessel to the narrowed location and then inflated to a fixed size using fluid (e.g. water) pressure of about 5 to 30 atmospheres. Typically, a balloon is inflated with sufficient pressure (4-12 atm) to fully expand the stenosis indentation (dumbbell or waist) of the partially inflated balloon. Occasionally, some calcified or highly fibrotic lesions require very high inflation pressures (>14 atm) to expand and eliminate the "dumbbell" appearance of the balloon. Overinflation of the balloon increases the risk of artery dissection. The inflated balloon forces open the obstruction comprised of white blood cell/clot and plaque deposits and expands surrounding muscular wall of the vessel, opening up the blood vessel for improved flow. The balloon is then deflated and withdrawn. A stent may or may not be inserted at the time of ballooning to ensure the vessel remains open.

A bifurcation lesion involves a clinically relevant side branch. Plaque may be located either in both branches or in the main vessel only or in the side branch only. The carina is the flow divider that lies between the main branch and side branch and is the region of high flow and high shear stress.

One angioplasty technique for plaque at a bifurcation is the "kissing balloon" technique. Noncompliant balloons, each having a balloon size that is about same size as the vessel (usually a slightly smaller diameter balloon for the side branch) are used. A balloon is first fed into the side branch so that it protrudes into the side branch and extends into the main branch, but not proximal to a stent. The balloon may be fed into a stent in the side branch. Another balloon (shorter than the main branch stent) is advanced to the main branch so it lies within the main branch but not extending beyond the confines of the stent in the main branch. The balloons are inflated simultaneously. Then the balloons are deflated simultaneously to avoid distortion. In a variation of the basic technique, the side branch balloon is inflated to high pressure (>20 atm, perhaps 24 or 26 atm) and then deflated. Then the main branch balloon is inflated to moderate pressure and deflated. Then, both balloons are simultaneously inflated at low pressure to correct any distortion caused by sequential balloon inflation. These procedures require the ability to independently inflate, maintain inflated, monitor pressure in, and deflate each balloon.

Unfortunately, devices available today do not provide the ability to independently inflate, maintain inflated, monitor pressure in, and deflate each balloon in a kissing balloon procedure. Instead, many practitioners use two separate indeflator devices to inflate, monitor and deflate each balloon independently. While effective, such an approach is not without problems. Managing two separate, but abutting, indeflators in limited available space, with several tubes extending to and from each indeflator, presents challenges to the practitioner and great risk of confusing one indeflator for the other.

One of the most costly components of an indeflator is the pressure gauge. Using two separate pressure gauges in an indeflator is not only costly, but requires a bulkier device. The additional bulkiness affects the weight, size and usability of the device.

Often it is not known if a second catheter is required for a procedure until the procedure is underway. A means for adding a "kissing balloon" catheter while a procedure is underway is needed.

Thus, what is needed is a device that facilitates independently supplying radiopaque contrast medium through one or more catheters, while independently inflating, monitoring and deflating up to two distal balloons using an adaptable device having a single shared pressure gauge, to which a second catheter can be added if and when needed.

SUMMARY OF THE INVENTION

An exemplary adaptable inflation device (indeflator), with one pressure guage, for up to two balloon catheters, for angioplasty includes a pump mechanism having a tubular reservoir with an outlet and a longitudinal axis, and a piston movable linearly through the tubular reservoir along the longitudinal axis, and a manually operated actuator coupled to the piston and controlling linear motion of the piston. A primary three-port valve has a first primary port in fluid communication with the outlet of the pump, a second primary port and a third primary port. The primary three port valve is switchable between a first state in which the first primary port, second primary port and third primary port are in fluid communication, and a second state in which the first primary port and second primary port are in fluid communication, and a third state in which the first primary port and third primary port are in fluid communication, and a fourth state in which the second primary port and third primary port are in fluid communication. A pressure gauge is in fluid communication with the second primary port of the primary three-port valve. A first outlet port, a second outlet port and a secondary three-port valve are between and in fluid communication with the pressure gauge and the first outlet port and the second outlet port. The secondary three-port valve has a first secondary port in fluid communication with primary three-port valve, a second secondary port and a third secondary port. The secondary three-port valve is switchable between a first state in which the first secondary port, second secondary port and third secondary port are in fluid communication, and a second state in which the first secondary port and second secondary port are in fluid communication, and a third state in which the first secondary port and third secondary port are in fluid communication. The first outlet port is in fluid communication with thee second secondary port of the secondary three-port valve. The first outlet port is attachable to a first catheter. The second outlet port is in fluid communication with the third secondary port of the secondary three-port valve. The second outlet port is attachable to the second catheter. An accessory port is fluidly coupled to the third primary port. The first outlet, second outlet and accessory pors are releasable fluid couplings, threaded and/or friction fit, e.g., Luer locks.

The manually operated actuator coupled to the piston of the pump mechanism may be a threaded shaft having one end coupled to the piston and a proximal end opposite the end coupled to the piston. A graspable rotatable handle is attached to the proximal end of the threaded shaft.

The pressure gauge may be permanently attached, threadedly engaged and removable, or attached by quick disconnect and replaceable. In the replaceable embodiments, the gauge may be replaced as desired to provide a different scale, units or other features. Ports and valve outlets may be correspondingly color coded.

In sum, an adaptable inflation device according to principles of the invention includes a plurality of three port valves controlling flow to two fluid channels each coupled at an outlet to a balloon catheter for angioplasty. A single in line pressure gauge, which may be removable, monitors pressure of each flow channel to each catheter. Each balloon catheter may be inflated and deflated, sequentially inflated, simultaneously inflated, sequentially deflated, simultaneously deflated, inflated to the same pressures, inflated to different pressures, partially deflated, and fully deflated. A second balloon catheter may be introduced at the outset of a procedure or when a procedure has already commenced.

Those skilled in the art will appreciate that the figures are not intended to be drawn to any particular scale; nor are the figures intended to illustrate every embodiment of the invention. The invention is not limited to the exemplary embodiments depicted in the figures or the specific components, steps, configurations, shapes, relative sizes, ornamental aspects or proportions as shown in the figures.

DETAILED DESCRIPTION

Figure 1:
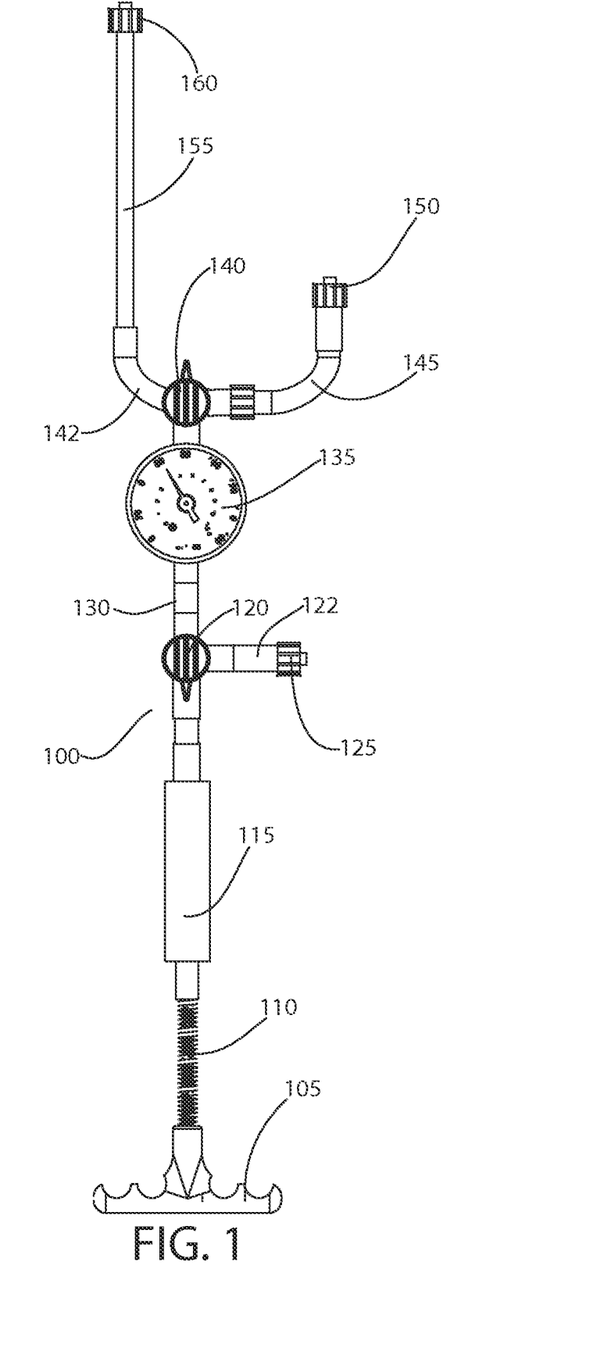
FIG. 1 provides a plan view of exemplary flow control components for an exemplary fluid dispensing and monitoring device for balloon angioplasty according to principles of the invention.

Referring to FIG. 1, an exemplary flow control assembly 100 for an exemplary fluid dispensing and monitoring device (i.e., inflator/deflator or "indeflator") for balloon angioplasty according to principles of the invention is conceptually illustrated. The assembly includes a pumping mechanism, i.e., a manually actuated fluid dispensing and aspirating mechanism 105-115, a pair of flow controlling stopcocks 120, 140, one of which is downstream of a pressure gauge 135 (i.e., distal to handle 105) and the other of which is upstream of the pressure gauge 135 (i.e., proximal to handle 105), and a plurality of ports 125, 150, 165, including an accessory port 125, a primary catheter port 160 and a secondary catheter port 150, with tubing 122, 130, 142, 145, 155 fluidly coupling the various components. Each of these components are described in greater detail below.

The exemplary pump, which is described in greater detail below with reference to FIGS. 12 and 13, comprises a tubular body 115 that contains a piston. The pump also includes a linear actuator. The linear actuator moves the piston within the tubular body 115. In the exemplary pump, the linear actuator comprises a threaded shaft or lead screw 110 and handle 105. Rotation of the lead screw in one direction causes the piston to move linearly in the tubular body 115 towards the stopcock 120. Rotation of the lead screw in the opposite direction causes the piston to move linearly in the tubular body 115 away from the stopcock 120. Linear motion of the plunger either urges fluid out of the tubular body 115 towards the stopcock 120 or draws fluid through the stopcock 120 into the tubular body 115.

The illustrated pump is merely one non-limiting example of a pump. Other pumping mechanisms known in the field of indeflators may be used in lieu of the illustrated pump without departing from the scope of the invention.

An indeflator, according to principles of the invention, includes a manifold attached to the outlet of the pump. An exemplary manifold is comprised of a three-port valve 120, also referred to herein as a stopcock 120, and a plurality of tubes 122, 130. One tube 122 of the manifold is fluidly coupled to an accessory port 125. The other tube 130 of the manifold is fluidly coupled to a pressure gauge 135. Each tube 122, 130 of the manifold comprises a fluid transmitting line or tube.

The three-port valve 120 is also referred to as a primary valve 120 to distinguish it from the other three-port valve 140, which is referred to as the secondary valve 140. The primary valve 120 controls fluid communication between the pump and each line (i.e., tube) 122, 130 of the manifold. Thus, valve 120 controls both flow past the pressure gauge 135 to the catheter lines and flow through the access port 125. In one position, the valve 120 allows flow to and from the pump through the valve 120 to and from the tube 130 in fluid communication with the pressure gauge 135. In another position, the valve 120 allows flow to and from tube 122 in fluid communication with accessory port 125. The valve 120 also includes an off position that blocks flow through the valve 120. The various positions are attained by rotating a control knob and attached valve stem of the valve 120 to a position corresponding to the desired setting.

Tube 122 leads from the primary valve 120 to an accessory port 125. The accessory port 125 is comprised of a releasable coupling, e.g., a Luer-Lock fitting, for accessory attachment. The accessory port 125 allows controlled evacuation of catheters, introduction of contrast media, saline, and wire guides as well as waste removal and attachment of catheters. Any port configuration suitable for mating with corresponding lines, devices and equipment (i.e., accessories) may be utilized. By way of example and not limitation, the port may comprise a Luer-Slip fitting that conforms to Luer taper dimensions configured to be pressed together with a mating fitting and held by friction.

The primary three-port valve 120 is optional. The invention may function without the primary three-port vale 120. In such an embodiment, the secondary three-port valve 140, downstream of the pressure gauge 135, may be used alone to control flow to and from each port 150 and 160. The secondary three-port valve 140 may be set to allow flow to and from port 150, to and from port 160, and to and from both port 150 and 160 simultaneously. The secondary three-port valve 140 may also be set to prevent flow to and from port 150, to and from port 160, and to and from both port 150 and 160 simultaneously. While optional, the primary three-port valve 120 provides the advantage of isolating the ports 150 and 160 and controlling flow to and from the accessory port 125.

Male and female coupling components are interchangeable. By way of example, a port may have a male coupling while a mating accessory has a female coupling, or vice versa. Thus, the invention is not limited to any particular arrangement of male and female couplings, so long as the couplings mate together to form a fluid flow path.

A pressure measuring instrument 135, such as a manometer, aneroid gauge, bourdon gauge, or an electronic pressure sensor (each a "pressure gauge"), is fluidly coupled to tube 130. The pressure gauge 135 senses and displays fluid pressure in the tube 130 over a useful range of pressures, such as from about 0 to 30 atmospheres. This range encompasses the pressures applied to inflate balloons in most angioplasty procedures. Another scale, e.g., psi, may also be displayed on the face of the primary measuring instrument. The static pressure measured by the pressure gauge 135 is the pressure in tube 130 and each other tube of the assembly in fluid communication with tube 130 at the time the pressure is measured. Fluid pressure in tube 130 may be the same as the fluid pressure in tube 142 and/or tube 145, either, both or none of which may be in fluid communication with tube 130, depending upon the configuration of the secondary valve 140.

In the exemplary embodiment, one pressure gauge 135 is provided for reading pressure in line 142 and line 145. Pressure in either line may be read by configuring the valve 140 to provide fluid communication with the desired line. Pressure in both lines may be read simultaneously by configuring the valve 140 to provide fluid communication with both lines. Consequently, pressure may be monitored independently in each catheter. Additionally, a different pressure may be applied in each catheter. Furthermore, pressure may be equilibrated between catheters. This may be accomplished using one pressure gauge 135.

Using one pressure gauge 135 for two separate catheters is advantageous, and a major improvement over prior art. An indeflator according to principles of the invention is typically disposable. The pressure gauge is a costly component and a source of bulkiness. Utilizing one pressure gauge instead of two or more, reduces size, cost and complexity, without compromising utility.

In one embodiment, the pressure gauge 135 is permanently attached. In another embodiment, the pressure gauge 135 may be removably attached. By way of example and not limitation, the pressure gauge may include a threaded male plug that mates with a female threaded socket. In this embodiment, the gauge may be replaced for a particular procedure. Thus, a gauge configured for readings between 1 and 30 atm may be replaced with a gauge configured for readings between 1 and 20 atm, with higher resolution. Similarly, a gauge configured for readings between 1 and 20 atm may be replaced with a gauge configured for readings between 1 and 30 atm, to facilitate a procedure that may require high pressure. If a gauge is defective, it may be replaced without discarding the entire device. In this manner, a pressure gauge of an indeflator according to principles of the invention may be replaced, selected and installed for a particular procedure.

An indeflator, according to principles of the invention, includes a manifold downstream of the pressure gauge 135. An exemplary manifold is comprised of a three-port valve 140 and a plurality of tubes 142, 145. One tube 142 of the manifold is fluidly coupled to primary catheter line 155 which terminates with a primary catheter port 160. The other tube 145 of the manifold is a secondary catheter tube 145 that terminates with a secondary catheter port 150. Each tube 142, 145 of the manifold comprises a fluid transmitting line or tube.

The three-port valve 140 is also referred to as a secondary valve 140 to distinguish it from the other three-port valve 120, which is referred to as the primary valve 120. The secondary valve 140 controls fluid communication between tube 130 and each line (i.e., tube) 142, 145 of the manifold downstream of the pressure gauge 135. In one position, the valve 140 allows flow to and from tube 130 through the valve 140 to and from the tube 142. In another position, the valve 140 allows flow to and from tube 130 through the valve 140 to and from the tube 145. In another position, the valve 140 allows flow to and from tube 130 through the valve 140 to and from tube 142 and tube 145. The valve 140 also includes an off position that blocks flow through the valve 140. The various positions are attained by rotating a control knob and attached valve stem of the valve 140 to a position corresponding to the desired setting.

Tube 142 leads from the secondary valve 140 to primary catheter line 155, which terminates with a primary catheter port 160. The catheter port 160 is comprised of a releasable coupling, e.g., a Luer-Lock fitting, for catheter attachment. Any port configuration suitable for mating with a corresponding catheter line and equipment may be utilized. Male and female coupling components are interchangeable. By way of example, a port may have a male coupling while a mating component has a female coupling, or vice versa. Thus, the invention is not limited to any particular arrangement of male and female couplings, so long as the couplings mate together to form a fluid pathway.

Tube 145 leads from the secondary valve 140 to secondary catheter port 150. The catheter port 150 is comprised of a releasable coupling, e.g., a Luer-Lock fitting, for catheter attachment. Any port configuration suitable for mating with a corresponding catheter line and equipment may be utilized. Male and female coupling components are interchangeable. By way of example, a port may have a male coupling while a mating component has a female coupling, or vice versa. Thus, the invention is not limited to any particular arrangement of male and female couplings, so long as the couplings mate together to form a fluid pathway.

Ports 150, 160 each allow attachment of a catheter. One or two catheters may be used. Until a procedure is underway with a first catheter, it is typically not known if a second catheter will be needed. Advantageously, a second catheter may be attached to one of the ports, while the first catheter is attached to the other port. Additionally, the second catheter may be attached and deployed intravenously while the first catheter is already attached, deployed and in use. Thus, the second catheter may be introduced if and when needed, even during a procedure already underway.

Figure 2:
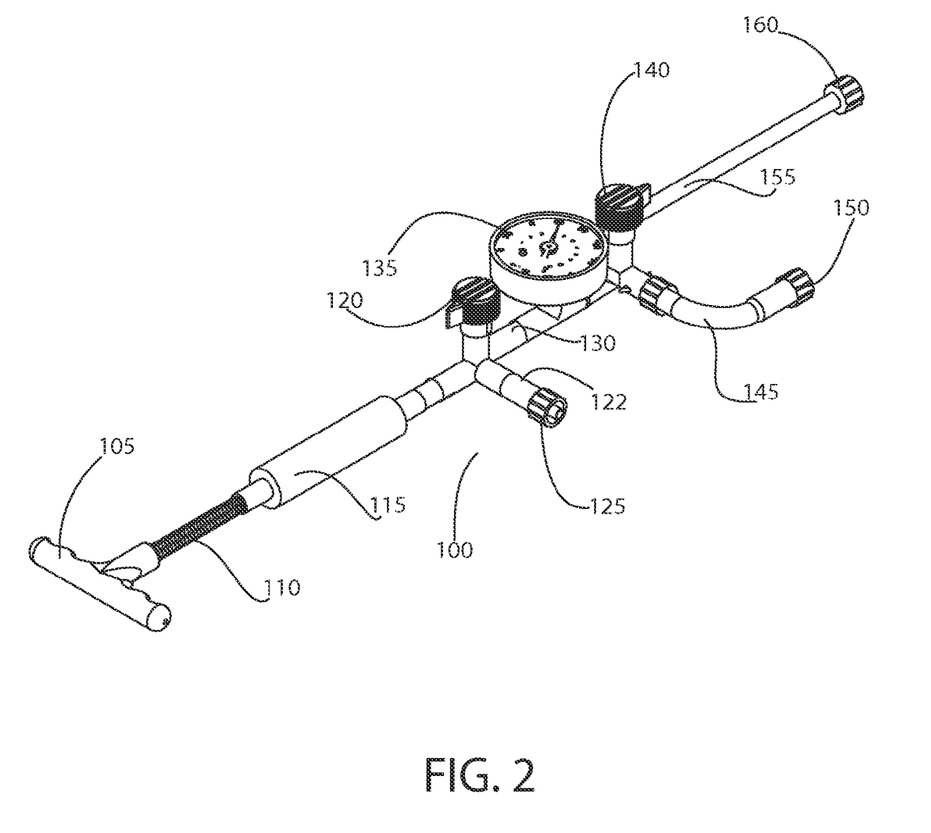
FIG. 2 provides a perspective view of exemplary flow control components for an exemplary fluid dispensing and monitoring device for balloon angioplasty according to principles of the invention.
Figure 3:
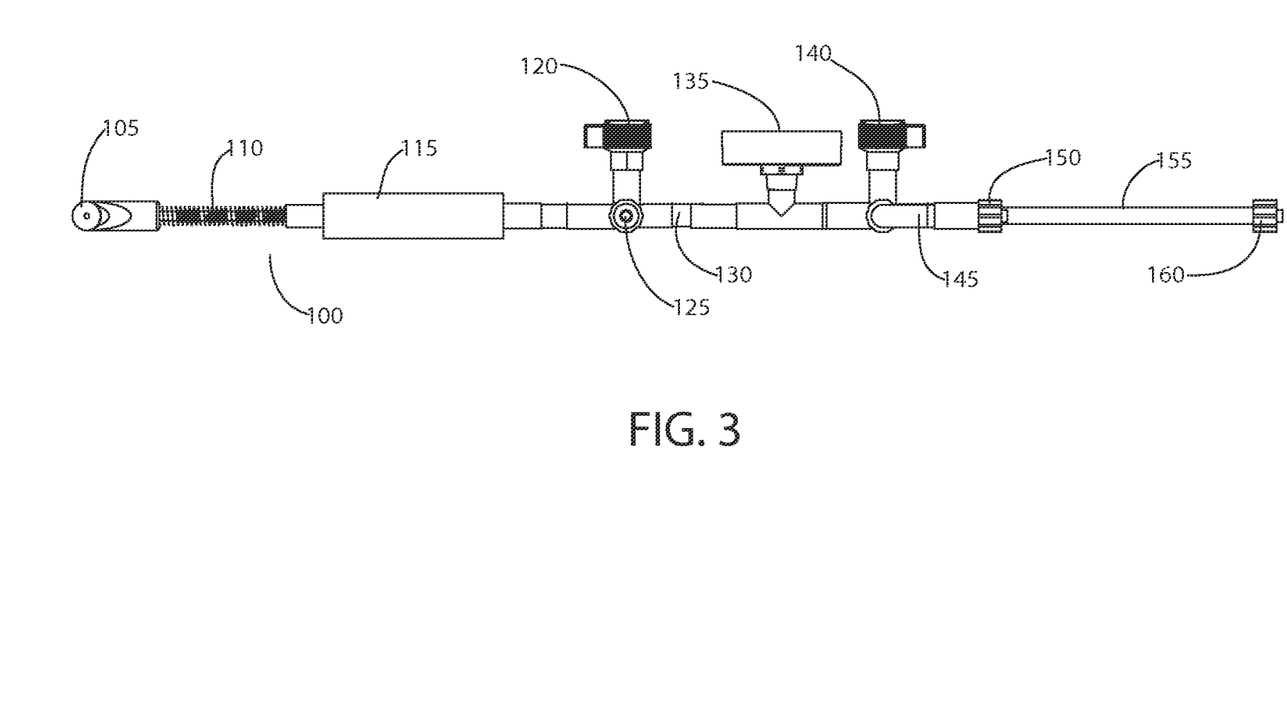
FIG. 3 provides a side view of exemplary flow control components for an exemplary fluid dispensing and monitoring device for balloon angioplasty according to principles of the invention.
Figure 4:
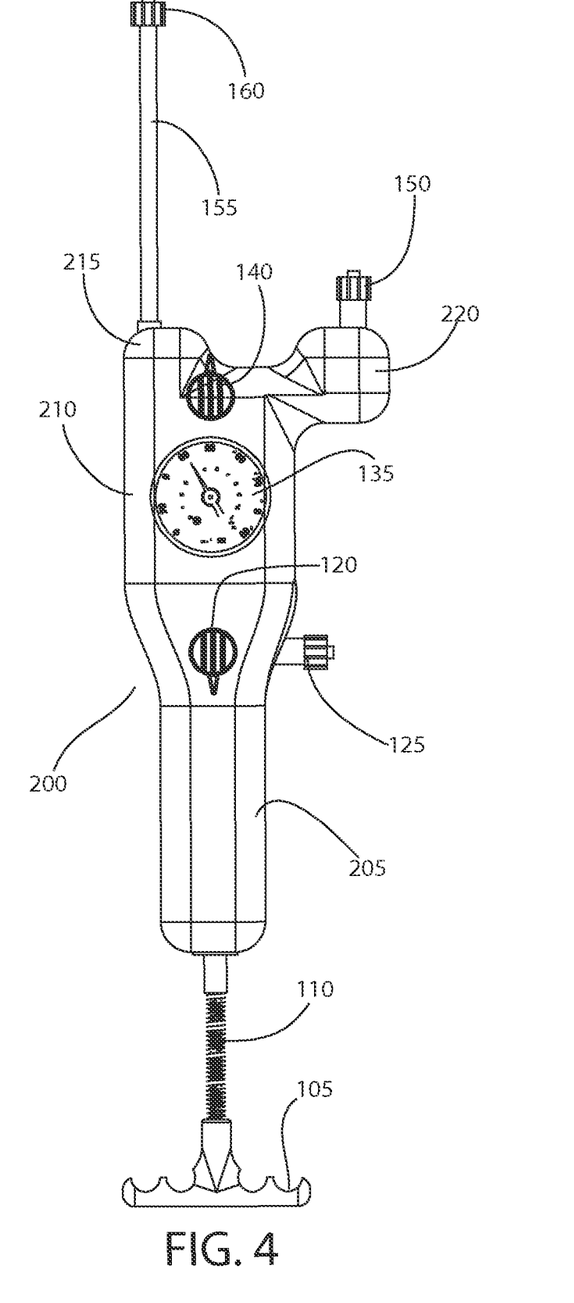
FIG. 4 provides a plan view of an exemplary dispensing and monitoring device for balloon angioplasty according to principles of the invention.
Figure 5:
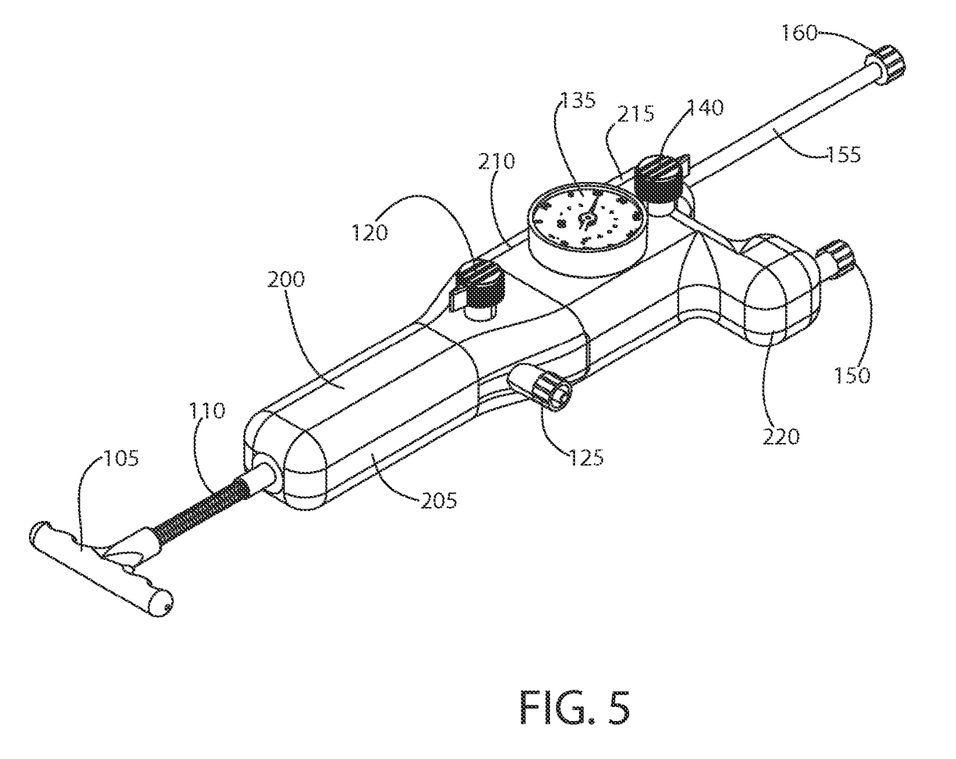
FIG. 5 provides a first perspective view of an exemplary dispensing and monitoring device for balloon angioplasty according to principles of the invention.
Figure 6:
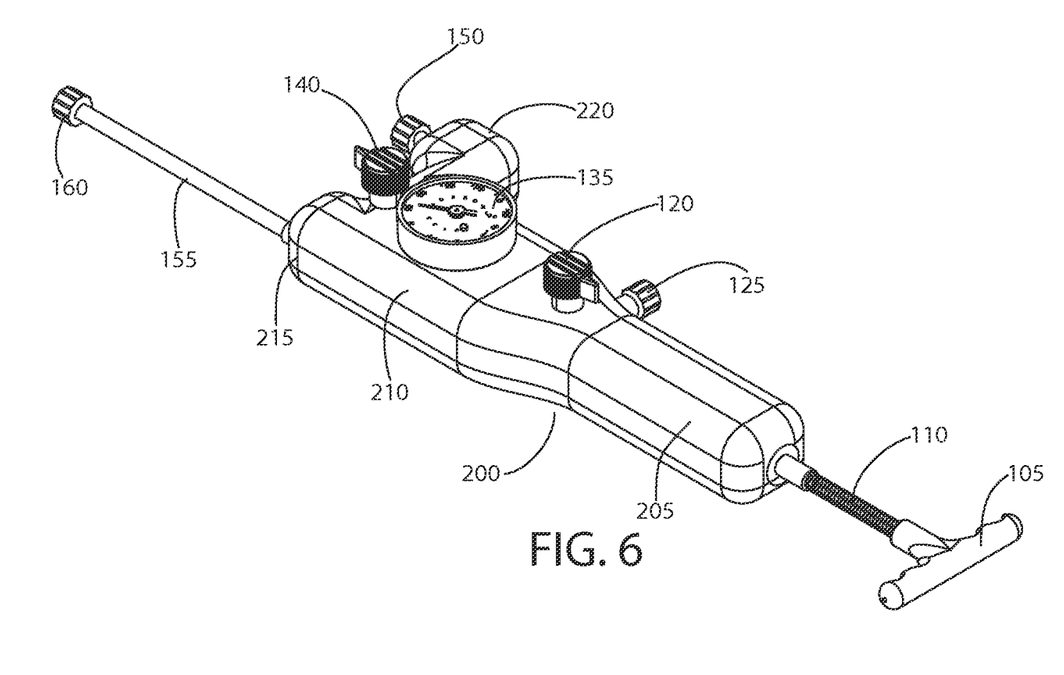
FIG. 6 provides a second perspective view of an exemplary dispensing and monitoring device for balloon angioplasty according to principles of the invention.
Figure 7:
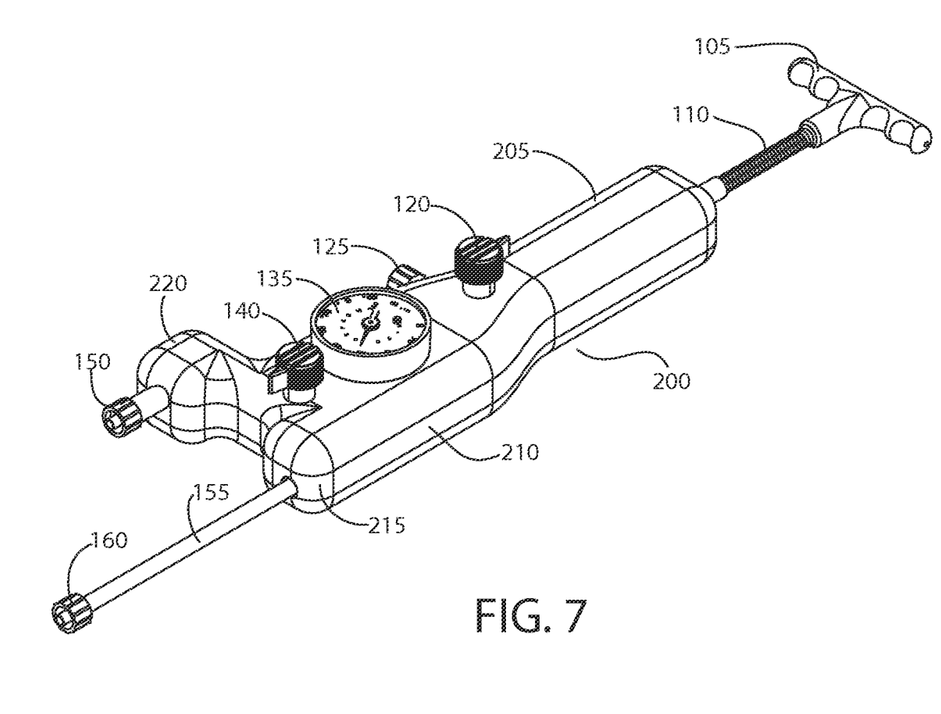
FIG. 7 provides a third perspective view of a primary catheter portion for an exemplary dispensing and monitoring device for balloon angioplasty according to principles of the invention.
Figure 8:
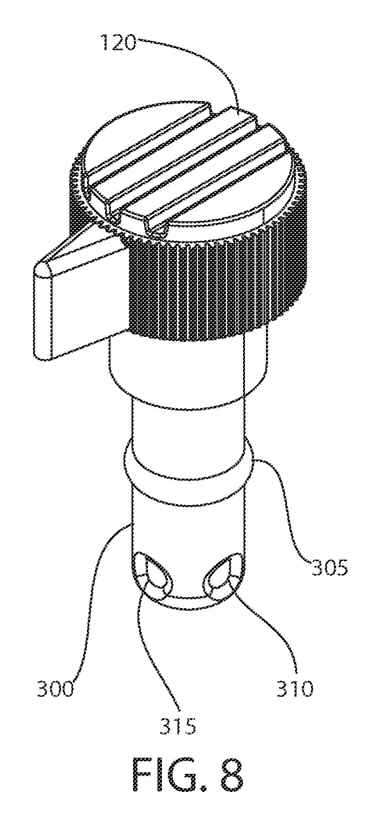
FIG. 8 provides a perspective view of an exemplary three-way valve for balloon angioplasty according to principles of the invention.

FIGS. 2 and 3 provide perspective and side views of the exemplary flow control components for the exemplary fluid dispensing and monitoring device 100 for balloon angioplasty according to principles of the invention. These views illustrate different elevations for the various components. The various elevations facilitate user access to certain components, while other components are contained in a housing. By way of example, manually adjustable control knobs of valves 120, 140 and the face of the pressure gauge are at a different elevation than the tubes.

FIGS. 4 through 7 provide various views of an exemplary dispensing and monitoring device 200 for balloon angioplasty according to principles of the invention. The device 200 includes the exemplary flow control assembly 100 described above with reference to FIGS. 1-3. A housing assembly, including a handle 205, a body 210, and terminals 215, 220, contains components of the flow control assembly 100.

The handle 205 of the housing 200, which is sized and shaped for gripping by a user, houses pump components, including, the tubular housing 115 and internal and downstream components of the pump. The threaded shaft 110 and handle 105 of the syringe-like pump assembly extend from the proximal end of the handle 205 of the housing 200. In the exemplary embodiment, portions of the primary valve 120 in line with tubing 122, 130 are contained in the handle, while a manually actuated control knob extends from the handle 205. However, the primary valve 120 may be located elsewhere, such as within the body 210 of the device 200. The accessory port 125 protrudes from a side of the handle 205.

The body 210 of the housing 200 contains components of the pressure gauge 135 and the secondary valve 140 that are in line with tubing 130, 142 and 145. The face of the gauge 135 is visible from the body 210, either by extending above the body 210 or being in a window of the body 210. The window may be a cavity that is sized and shaped to receive the gauge 135 and is uncovered or covered with a transparent lens. In the exemplary embodiment, portions of the secondary valve 140 in line with tubing 142, 145 are also contained in the body 210, while a manually actuated control knob extends from the body 210.

The primary catheter line 155 which terminates with a primary catheter port 160, extends from the distal end of the first terminal 215 of the housing 200. The secondary catheter tube 145 that terminates with a secondary catheter port 150, extends from the distal end of the second terminal 220 of the housing 200.

Before using a balloon catheter, the catheter is substantially evacuated. The accessory port 125 may be used to evacuate air from attached balloon catheters. An evacuated syringe may be attached to the accessory port 125, via releasable coupling, with the primary valve 120 and secondary valve 140 set to allow fluid communication between the accessory port 125 and a catheter to be evacuated. By aspiration through the syringe, a negative pressure may be applied to the accessory port 125. Air from an attached balloon catheter is drawn through the accessory port 125. After one catheter is evacuated, a second catheter may be evacuated by setting the secondary valve 140 to allow fluid communication between the accessory port 125 and the second catheter to be evacuated, while preventing flow to the catheter that has already been evacuated. These steps may be repeated if further aspiration is necessary to sufficiently evacuate each balloon catheter before inflation fluid is introduced. Other evacuation techniques may be implemented through the accessory port 125 and valves 120, 140. Thus, the invention facilitates evacuation of each attached balloon catheter and maintains each evacuated balloon catheter in a substantially evacuated state until an inflating fluid is introduced.

Figure 14:
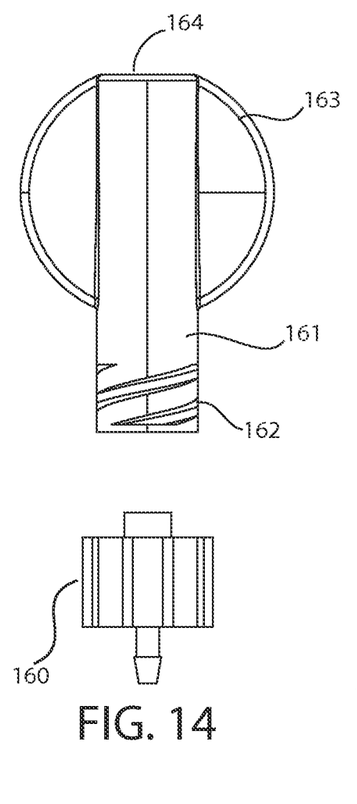
FIG. 14 provides a plan view of of an exemplary Luer-Lock fitting for an exemplary dispensing and monitoring device for balloon angioplasty according to principles of the invention.
Figure 15:
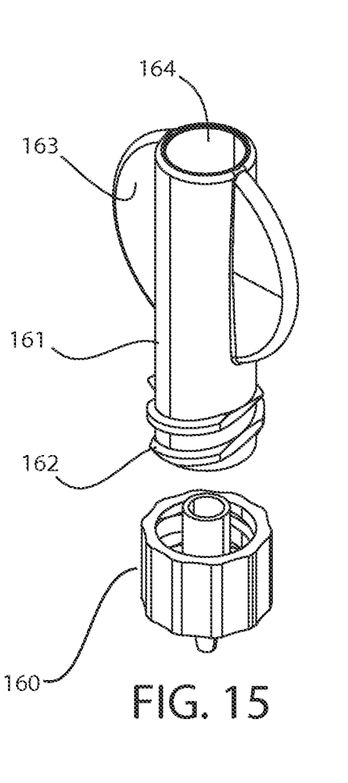
FIG. 15 provides a perspective view of of an exemplary Luer-Lock fitting for an exemplary dispensing and monitoring device for balloon angioplasty according to principles of the invention.

In an exemplary implementation, ports 150, 160 are Luer-Lock fittings, suitable for attachment to a balloon catheter for angioplasty. As conceptually illustrated in FIGS. 14 and 15, an exemplary Luer-Lock fitting may be securely joined by means of a tabbed 163 threaded 166 hub 161 on a female fitting (e.g., the fitting on the end of the line or equipment to be attached, such as the catheter) with an outlet 164 coupled to the attached line or equipment. The female fitting screws into threads in a sleeve 160 on a male fitting (e.g., the port). The sleeve 160 may be rotatable relative to a tube to which it is coupled. Rotation of the sleeve 160 allows connection to a threaded mating member 162, without twisting and kinking of tubing.

Figure 16:
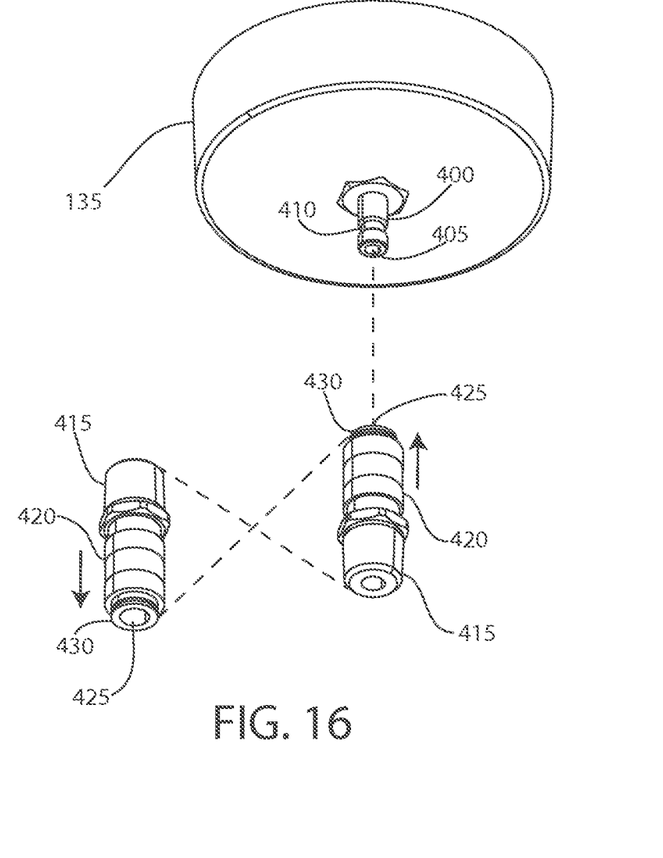
FIG. 16 conceptually illustrates a pressure gauge with an optional quick disconnect coupling for releasable attachment to a dispensing and monitoring device for balloon angioplasty according to principles of the invention.

As an alternative to the threaded fitting as described above, a quick connect coupling may be used to provide a fast, make-or-break connection between the pressure gauge 135 and the tubing to which the gauge 135 is fluidly coupled. In one embodiment, as conceptually illustrated in FIG. 16, a quick connect coupling comprised of a female fitting 415 and a mating male fitting 400 may be provided. The male fitting 400, which is comprised of a tube 405 with a recessed collar 410, extends from the pressure gauge 135 to provide fluid communication to the pressure gauge 135 through the tube 405. The tube 405 is shaped and sized to mate with the female fitting 415 in fluid communication with tubing of the flow control assembly 100. The female fitting 415 has an elastomeric diaphragm that provides a leak-proof seal until the diaphragm is pushed open by the end of the tube 405 of the male fitting 400. A movable outer collar 420 is biased in a position on the female fitting 415 by a spring. When the tube 405 of the male fitting 400 is inserted into the mating channel 425 of the female fitting 415, a ring of ball bearings held beneath the movable outer collar 420 engages the recessed collar 410 of the male fitting 400 and holds the male fitting 400 in place. To release the male fitting 400, the collar 420 is moved in a direction opposed to the spring bias, e.g., forward (towards the free end 430 of the female fitting), thereby releasing the ring of ball bearings from the recessed collar 410. When the male fitting 400 is removed, the diaphragm closes and prevents fluid from escaping from the female fitting 415. In this embodiment, sufficient space is provided between the bottom of the pressure gauge 135 and the corresponding surface of the body 210 of the housing 200 to allow a user to grip and manipulate the movable collar 420 with the user's fingers.

Referring now to FIGS. 8 through 11, various views of an exemplary valve stem assembly for an exemplary dispensing and monitoring device for balloon angioplasty with two balloon catheters according to principles of the invention is conceptually illustrated. An exemplary three port valve comprises a rotatable valve stem 300 with a T-shaped fluid passage comprised of converging channels 310, 315, 320 extending through the stem in a T-shaped configuration. Openings of the T-shaped fluid passage defined by the channels 310, 315, 320 may be rotated into alignment with the three ports of each three port valve, such as ports into tubing 116, 122, 130 for valve 120. As the valve stem 300 is rotated, the openings move into and out of alignment with a port, thereby opening or sealing the port. A toroidal O-ring 305 sits in a depression on the stem and a corresponding depression in the tubular housing of the valve to provide a fluid-tight seal. A three port valve according to principles of the invention allows all three ports to be opened and in fluid communication and two ports to be open and in fluid communication. In embodiments where the ports into tubing are sized and positioned such that a turn of the valve stem that is less than 90° (e.g., a 45° turn) places all tubing ports out of alignment with the valve ports, then all ports may be blocked. The invention is not limited to a particular three port valve. Valves and valve assemblies other than the exemplary manual three port valve described herein may be utilized without departing from the scope of the invention.

Figures 9, 10, 11:
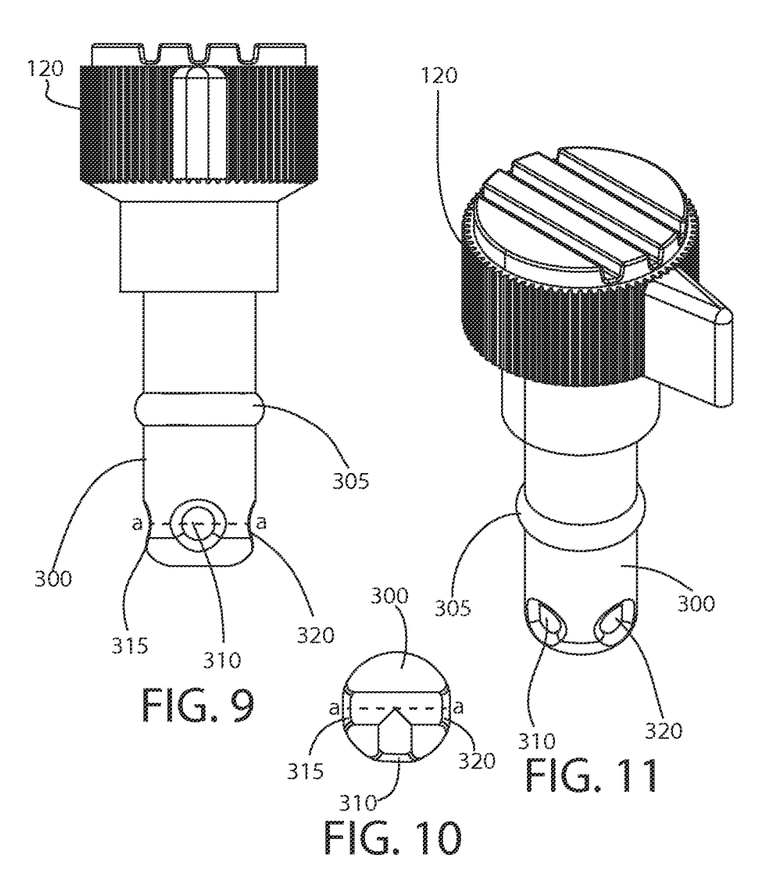
FIG. 9 provides a front view of an exemplary three-way valve for balloon angioplasty according to principles of the invention.
FIG. 10 provides a section view (a-a) of a portion of an exemplary three-way valve for balloon angioplasty according to principles of the invention.
FIG. 11 provides a perspective view of an exemplary three-way valve for balloon angioplasty according to principles of the invention.

In an alternative implementation, certain three-port valves may have a rotatable valve stem with an L-shaped fluid passage extending through the stem, instead of the T-shaped passage shown in FIG. 10. In this embodiment, only two orthogonal ports can be in fluid communication with the L-shaped fluid passage at a time.

The invention includes a manually actuated syringe-like pump to inject fluid. The invention is not limited to a particular pump. Rather any pump suitable for dispensing fluid in a controlled manner for use in an indeflator for inflating a balloon of a balloon catheter for angioplasty may be utilized, with the caveat that the plump have a volumetric pumping capacity to provide sufficient fluid to inflate two separate balloon catheters and further that the pump support the required range of pressures for inflation.

Figure 12:
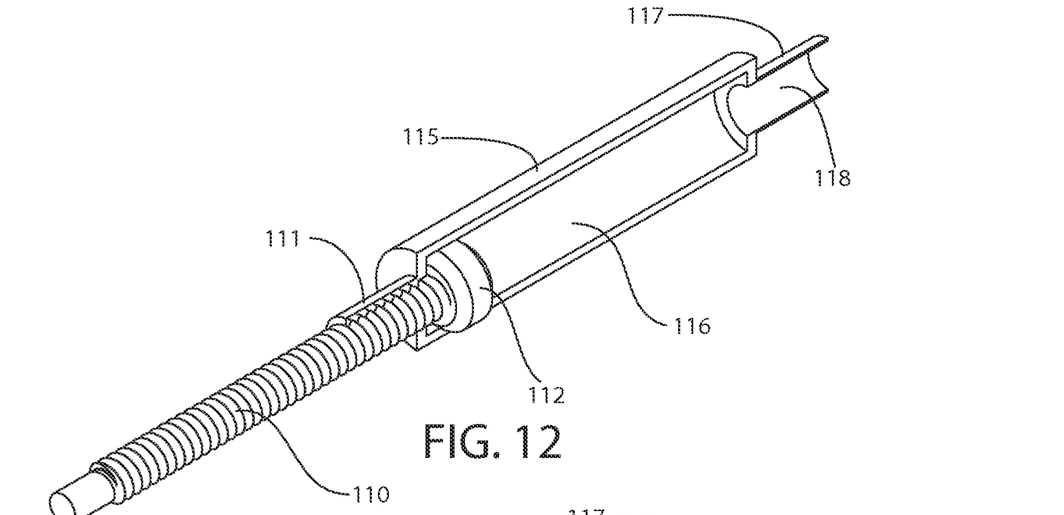
FIG. 12 provides a perspective view of a cutaway portion of an exemplary plunger in a first state for balloon angioplasty according to principles of the invention.
Figure 13:
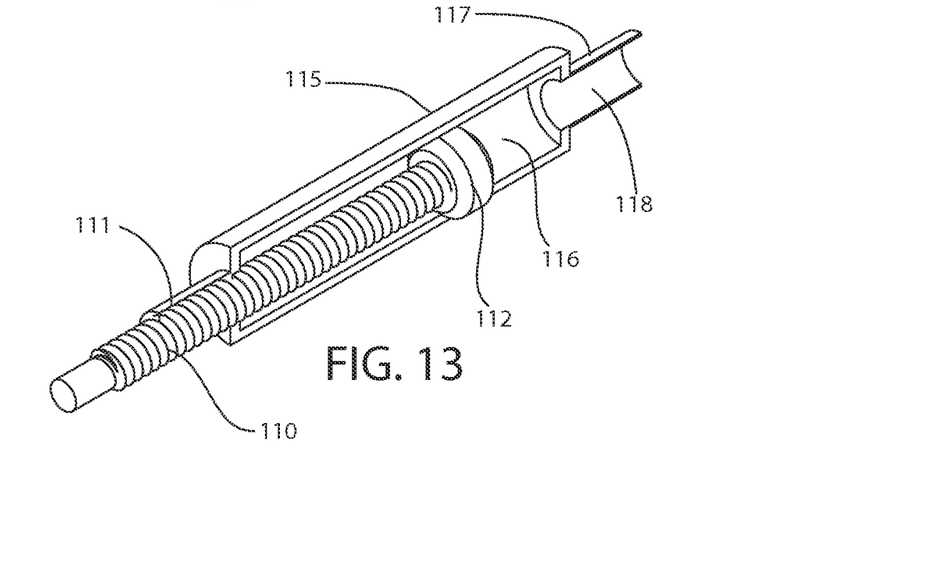
FIG. 13 provides a perspective view of a cutaway portion of an exemplary plunger in a second state for balloon angioplasty according to principles of the invention.

With reference to FIGS. 12 and 13, an exemplary pump comprises a tubular body 115 with an outlet 117 at the distal end. The body 115 defines a chamber 116. The outlet 117 defines an outlet channel 118. A piston 112 disposed in the chamber 116 of the tubular body 115 is movable linearly within the chamber 116 along the longitudinal axis of the body 120. The periphery of the piston 112 provides a fluid seal against the interior surface of the tubular body 115. A shaft, such as threaded shaft 110, extends from the piston 112. The threaded shaft 110 is threadedly received by a threaded bushing 111 at the proximal end of the tubular body 115 opposite the outlet 117. An actuator knob or ergonomic handle 105 (FIGS. 1-7) is attached to the end of the threaded shaft 110 that is opposite the piston 112. Rotation of the knob 105 in one direction, causes the threaded shaft 110 to rotate in the same direction and advances the piston 112 in the chamber 116 of the tubular body 115 towards the channel 118 of outlet 117. Rotation of the handle 105 in the other direction, causes the threaded shaft 110 to rotate and moves the piston in the chamber 116 of the tubular body 115 away from the outlet 117. Advancement of the piston 112 towards the outlet 117 produces a positive pressure that expels fluid ahead of the piston 112 through the chamber 116 of the tubular body 115 through the channel 118 of the outlet 117. Retreating motion of the piston 112 away from the outlet 117 produces a negative pressure differential that draws fluid into the chamber 116 of the tubular body 115 through the chamber 118 of the outlet 117. One or more releasable locks may be provided to releasably lock the shaft in a particular position.

To fill the pump with a fluid (e.g., saline), a saline source may be fluidly coupled to a port, such as, but not limited to, accessory port 125. The primary valve 120 may be configured to allow fluid communication between the accessory port 125 and the pump housing 115. When the primary valve 120 is set to allow fluid communication between the accessory port 125, and the pump outlet 117, then, as the piston 112 is moved away from the outlet 117, fluid is drawn through the outlet channel 118 into the chamber 116 of the tubular body 115 between the piston 112 and the outlet channel 118. Similarly, fluid may be drawn into the pump via ports 150 and 160.

After the pump of the indeflator is filled with a sufficient volume of fluid for inflating one or two balloon catheters, the indeflator may be configured for inflation. For sequential inflation, fluid is forced through ports 150 and 160. For example, primary valve 120 may be set to allow flow from the pump through line 130 to secondary valve 140, while secondary valve 140 may be configured to allow flow through line 142 and/or line 145 to port 160 and/or port 150. Primary valve 120 may be configured to allow flow from port 132 to port 133. Advancing the piston 112 towards the outlet 117 forces fluid from the pump to either or both of ports 150, 160, to each of which a balloon catheter may be attached. The pressure gauge 155 monitors pressure in the line 130 and fluidly coupled lines 142 and 145. When the desired pressure is reached, secondary valve 140 may be set to prevent fluid flow from line 142 and/or 145 through valve 140. Thus, elevated pressure in line 142 and/or 145, and consequently any balloon catheter attached to a port 150 and/or 160, can be maintained. Furthermore, while pressure is maintained in one catheter attached to one port, such as port 160, a second catheter may be omitted or added to port 150 and separately inflated, deflated, attached or detached. To do so, secondary valve 160 may be set to allow flow from line 130 to line 145, but not to line 155. Primary valve 120 may be configured to allow flow from the pump through line 130. Advancing the piston 112 towards the outlet 117 forces fluid from the pump through 130 to line 145 and out of the outlet port 150, to which a balloon catheter may be connected. The pressure gauge 135 monitors pressure in line 130 and fluidly coupled line 145. When the desired pressure is reached, secondary valve 140 may be set to prevent flow from line 130 to line 145, as well as from line 130 to line 155. In this manner, elevated pressure in each catheter attached to ports 150 and 160 will be maintained.

Subsequently, the inflated balloon catheters may be deflated simultaneously or sequentially. In sequential deflation, the pressurized fluid may be exhausted through each port 150, 160 to which a catheter is attached. The fluid may flow through lines 145 and/or 155 through valve 140, through line 130, through calve 120, to the pump and/or to accessory port 125 to which an evacuation device (e.g., syringe) may be attached.

For simultaneous kissing balloon inflation, valves 120 and 140 may be configured to allow flow from the pump to both outlet ports 150, 160, to which catheters may be attached. In this manner, each balloon catheter may be inflated and deflated, sequentially inflated, simultaneously inflated, sequentially deflated, simultaneously deflated, inflated to the same pressures, inflated to different pressures, partially deflated, and fully deflated. Pressure in each balloon catheter may be monitored. Through accessory port 125 fluids (e.g., saline or contrast media) may be introduced into or evacuated from a balloon catheter. Pressure gauges may be fixed and may be identical or different. Alternatively, pressure gauges may be removable and the same or different. Pressure gauges may be removed and replaced. Fluids (e.g., saline or contrast media) may be introduced or added to the pump and branches, even during a procedure, without deflating a catheter. An indeflator according to principles of the invention thus provides enhanced versatility over conventional indeflators, which do not facilitate simultaneous inflation or deflation, and do not allow removal of pressure gauges, and do not allow inflation and deflation of both balloon catheters through a single pump.

Various ergonomic contours, grips and angles may be applied to increase gripping, manipulating and viewing comfort, without departing from the scope of the invention. Such features may include molded or attached padding to the handle, contours to the handle and knobs, an angled arrangement of the pressure gauge to enhance viewing, transparent plastics to enhance viewing of contents of the pump and/or tubing. These features and other ergonomic and aesthetic features known in the art are intended to come within the scope of the invention.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

The invention claimed is:

1. An adaptable inflation device for up to two balloon catheters for angioplasty, said two balloon catheters including a first catheter and a second catheter, said adaptable inflation device comprising:
   a pump mechanism having a tubular reservoir with an outlet and a longitudinal axis, and piston movable linearly through the tubular reservoir along the longitudinal axis, and a manually operated actuator coupled to said piston and controlling linear motion of the piston; and
   a primary three-port valve having a first primary port in fluid communication with the outlet of the pump, a second primary port and a third primary port, said primary three port valve being switchable between a first state in which the first primary port, second primary port and third primary port are in fluid communication, and a second state in which the first primary port and second primary port are in fluid communication, and a third state in which the first primary port and third primary port are in fluid communication, and a fourth state in which the second primary port and third primary port are in fluid communication; and
   a pressure gauge in fluid communication with the second primary port of the primary three-port valve; and
   a first outlet port, a second outlet port and a secondary three-port valve between and in fluid communication with the pressure gauge and the first outlet port and the second outlet port, the pressure gauge being disposed between the primary three-port valve and the secondary three-point valve;
   the secondary three-port valve having a first secondary port in fluid communication with primary three-port valve, a second secondary port and a third secondary port, said secondary three-port valve being switchable between a first state in which the first secondary port, second secondary port and third secondary port are in fluid communication, and a second state in which the first secondary port and second secondary port are in fluid communication, and a third state in which the first secondary port and third secondary port are in fluid communication; and
   the first outlet port being in fluid communication with second secondary port of the secondary three-port valve, said first outlet port being attached to the first catheter; and
   the second outlet port in fluid communication with the third secondary port of the secondary three-port valve, said second outlet port being attached to the second catheter.

2. The adaptable inflation device for up to two balloon catheters for angioplasty according to claim 1, further comprising an accessory port fluidly coupled to the third primary port.

3. The adaptable inflation device for up to two balloon catheters for angioplasty according to claim 2, the first outlet port comprising a releasable fluid coupling.

4. The adaptable inflation device for up to two balloon catheters for angioplasty according to claim 2, the second outlet port comprising a releasable fluid coupling.

5. The adaptable inflation device for up to two balloon catheters for angioplasty according to claim 2, the accessory port comprising a releasable fluid coupling.

6. The adaptable inflation device for up to two balloon catheters for angioplasty according to claim 2, the accessory port being fluidly coupled to a syringe.

7. The adaptable inflation device for up to two balloon catheters for angioplasty according to claim 1, said first outlet port comprising a threaded fluid fitting.

8. The adaptable inflation device for up to two balloon catheters for angioplasty according to claim 7, said second outlet port comprising a threaded fluid fitting.

9. The adaptable inflation device for up to two balloon catheters for angioplasty according to claim 1, said accessory port comprising a threaded fluid fitting.

10. The adaptable inflation device for up to two balloon catheters for angioplasty according to claim 1, the first outlet port comprising a first Luer Lock fitting and the second outlet port comprising a second Luer Lock fitting.

11. The adaptable inflation device for up to two balloon catheters for angioplasty according to claim 1, said manually operated actuator coupled to said piston of said pump mechanism comprising a threaded shaft having one end coupled to said piston and a proximal end opposite the end coupled to the piston.

12. The adaptable inflation device for up to two balloon catheters for angioplasty according to claim 11, said manually operated actuator further comprising a graspable rotatable handle attached to the proximal end of the threaded shaft.

13. The adaptable inflation device for up to two balloon catheters for angioplasty according to claim 1, said pressure gauge being threadedly engaged and removable.

14. The adaptable inflation device for up to two balloon catheters for angioplasty according to claim 1, further comprising:
   a first fluid flow line fluidly coupled to the second primary port of the primary three-port valve
   a first quick disconnect coupling fluidly coupling said pressure gauge to the first fluid flow line fluidly coupled to the second primary port of the primary three-port valve.

15. The adaptable inflation device for up to two balloon catheters for angioplasty according to claim 1, further comprising:
   a first fluid flow line fluidly coupled to the second primary port of the primary three-port valve;
   a first threaded coupling fluidly coupling said pressure gauge to the first fluid flow line fluidly coupled to the second primary port of the primary three-port valve.

16. The adaptable inflation device for up to two balloon catheters for angioplasty according to claim 2, said first outlet port being a first color, and said second outlet port being a second color and the secondary three-port valve being correspondingly color-coded.

17. The adaptable inflation device for up to two balloon catheters for angioplasty according to claim 1, said primary three-port valve switched to allow simultaneous inflation and deflation of the first catheter and the second catheter through the first outlet port and the second outlet port respectively.

18. The adaptable inflation device for up to two balloon catheters for angioplasty according to claim 1, said primary three-port valve switched to allow inflation and deflation of one of the first catheter through the first outlet port and the second catheter through the second outlet port, but to not allow inflation of the other of the first catheter through the first outlet port and the second catheter through the second outlet port.

* * * * *